US010836196B2

(12) United States Patent
Warner et al.

(10) Patent No.: US 10,836,196 B2
(45) Date of Patent: *Nov. 17, 2020

(54) SUBSTRATES HAVING IMPROVED CROCKFASTNESS

(71) Applicant: The Procter & Gamble Company, Cincinnati, OH (US)

(72) Inventors: Alrick Vincent Warner, Loveland, OH (US); Timothy Wayne Robertson, Cincinnati, OH (US); Wenbin Li, Mason, OH (US); Charles Douglas Mccurry, Morganton, NC (US)

(73) Assignee: The Procter & Gamble Company, Cincinnati, OH (US)

( * ) Notice: Subject to any disclaimer, the term of this patent is extended or adjusted under 35 U.S.C. 154(b) by 273 days.

This patent is subject to a terminal disclaimer.

(21) Appl. No.: 15/682,596

(22) Filed: Aug. 22, 2017

(65) Prior Publication Data

US 2017/0348164 A1    Dec. 7, 2017

Related U.S. Application Data

(60) Continuation of application No. 15/008,548, filed on Jan. 28, 2016, now Pat. No. 9,770,373, which is a continuation of application No. 14/164,357, filed on Jan. 27, 2014, now Pat. No. 9,283,794, which is a continuation of application No. 13/476,078, filed on May 21, 2012, now Pat. No. 8,673,430, which is a
(Continued)

(51) Int. Cl.
*B41M 5/52* (2006.01)
*B32B 5/02* (2006.01)
*B41M 5/50* (2006.01)

(52) U.S. Cl.
CPC .............. *B41M 5/52* (2013.01); *B32B 5/024* (2013.01); *B41M 5/508* (2013.01); *B41M 5/5218* (2013.01); *B41M 5/5254* (2013.01); *Y10T 428/24802* (2015.01); *Y10T 428/25* (2015.01)

(58) Field of Classification Search
CPC .... B41M 5/52; B41M 5/5254; B41M 5/5218; B41M 5/44; B41M 5/42; B41M 3/00; G11B 5/708; G11B 5/735; G11B 5/738; G11B 7/24
USPC ......................................................... 428/32.1
See application file for complete search history.

(56) References Cited

U.S. PATENT DOCUMENTS 3,860,003 A    1/1975  Buell
3,950,290 A    4/1976  Drury et al.
(Continued)

FOREIGN PATENT DOCUMENTS

DE            103 48 260 A1    5/2005
DE       10 2005 045375 A1    3/2007
(Continued)

OTHER PUBLICATIONS

Sigma Aldrich "Polymer Product From Aldrich", pp. 52-53.
(Continued)

*Primary Examiner* — Betelhem Shewareged
(74) *Attorney, Agent, or Firm* — Daniel S. Albrecht; Wednesday G. Shipp (57) ABSTRACT

An ink-printed substrate includes a substrate and water-based ink composition printed on the substrate, and has a Crockfastness-Loss-to-Density Ratio of about −1.0 to about −6.0.

20 Claims, 4 Drawing Sheets

Related U.S. Application Data division of application No. 12/372,957, filed on Feb. 18, 2009, now Pat. No. 8,216,666.

(60) Provisional application No. 61/032,627, filed on Feb. 29, 2008.

(56) References Cited

U.S. PATENT DOCUMENTS

| | | |
|---|---|---|
| 4,173,554 A | 11/1979 | Sulzberg |
| 4,610,678 A | 9/1986 | Weisman et al. |
| 4,834,735 A | 5/1989 | Alemany et al. |
| 4,888,231 A | 12/1989 | Angstadt |
| 4,940,464 A | 7/1990 | Van Gompel et al. |
| 5,037,416 A | 8/1991 | Allen et al. |
| 5,085,698 A | 2/1992 | Ma et al. |
| 5,092,861 A | 3/1992 | Nomura et al. |
| 5,151,092 A | 9/1992 | Buell et al. |
| 5,246,433 A | 9/1993 | Hasse et al. |
| 5,260,345 A | 11/1993 | DesMarais et al. |
| 5,269,775 A | 12/1993 | Freeland et al. |
| 5,387,207 A | 2/1995 | Dyer et al. |
| 5,397,316 A | 3/1995 | LaVon et al. |
| 5,458,590 A | 10/1995 | Schleing et al. |
| 5,554,145 A | 9/1996 | Roe et al. |
| 5,569,234 A | 10/1996 | Buell et al. |
| 5,571,096 A | 11/1996 | Dobrin et al. |
| 5,625,222 A | 4/1997 | Yoneda et al. |
| 5,744,001 A | 4/1998 | Lineheart et al. |
| 5,853,859 A | 12/1998 | Levy et al. |
| 5,897,545 A | 4/1999 | Kline et al. |
| 5,957,908 A | 9/1999 | Kline et al. |
| 6,004,306 A | 12/1999 | Robles et al. |
| 6,120,487 A | 9/2000 | Ashton |
| 6,120,489 A | 9/2000 | Johnson et al. |
| 6,566,426 B1 | 5/2003 | Kanaida et al. |
| 6,613,403 B2 | 9/2003 | Tan et al. |
| 6,905,732 B1 | 6/2005 | Dunshee et al. |
| 7,141,617 B2 | 11/2006 | Gratson et al. |
| 7,534,830 B2 | 5/2009 | Williams |
| 8,216,666 B2 | 7/2012 | Warner et al. |
| 8,673,430 B2 | 3/2014 | Warner et al. |
| 9,283,794 B2 | 3/2016 | Warner et al. |
| 9,770,373 B2 * | 9/2017 | Warner ............. A61F 13/15203 |
| 2001/0035110 A1 | 11/2001 | Kato |
| 2003/0008938 A1 | 1/2003 | Sano et al. |
| 2003/0029355 A1 | 2/2003 | Miyabayashi |
| 2003/0046770 A1 | 3/2003 | Sanduja et al. |
| 2003/0203695 A1 * | 10/2003 | Polanco .................... D01F 1/10 442/365 |
| 2003/0207091 A1 | 11/2003 | Nair et al. |
| 2003/0212200 A1 | 11/2003 | Bellas |
| 2003/0233082 A1 | 12/2003 | Kline et al. |
| 2004/0017075 A1 * | 1/2004 | Knoerzer ................. B41M 3/00 283/72 |
| 2004/0086678 A1 | 5/2004 | Chen et al. |
| 2004/0180151 A1 | 9/2004 | Sen |
| 2004/0192808 A1 | 9/2004 | Ohno et al. |
| 2004/0196346 A1 | 10/2004 | Redding et al. |
| 2005/0059769 A1 | 3/2005 | Chou et al. |
| 2005/0070629 A1 | 3/2005 | Roberts |
| 2005/0087104 A1 | 4/2005 | Nguyen |
| 2005/0182154 A1 | 8/2005 | Berge et al. |
| 2006/0068666 A1 | 3/2006 | Sharma et al. |
| 2006/0246263 A1 | 11/2006 | Yahiaoui et al. |
| 2007/0066709 A1 | 3/2007 | Chen et al. |
| 2007/0100025 A1 | 5/2007 | Steiner et al. |
| 2007/0269740 A1 | 11/2007 | Blank et al. |
| 2008/0085384 A1 | 4/2008 | Ylitalo et al. |
| 2008/0227356 A1 | 9/2008 | Poruthoor et al. |
| 2009/0220751 A1 | 9/2009 | Warner et al. |
| 2009/0221736 A1 | 9/2009 | McCurry |
| 2012/0232509 A1 | 9/2012 | Warner et al. |
| 2014/0309608 A1 | 10/2014 | Warner et al. |

FOREIGN PATENT DOCUMENTS

| | | | |
|---|---|---|---|
| EP | 0 687 325 B1 | 7/1996 | |
| EP | 1 431 321 A1 | 6/2004 | |
| EP | 2657308 A1 * | 10/2013 | ........... C09D 175/16 |
| GB | 1325615 A | 8/1973 | |
| GB | 1351976 A | 5/1974 | |
| JP | 2993113 B2 | 10/1999 | |
| JP | 2003-336179 A | 11/2003 | |
| JP | 3620671 B2 | 2/2005 | |
| JP | 2009-242561 | 10/2009 | |
| JP | 2016-083922 | 5/2016 | |
| WO | WO 95/16746 | 6/1995 | |
| WO | WO 01/83626 A1 | 11/2001 | |
| WO | WO 02/24757 A2 | 3/2002 | |
| WO | WO 03/062334 A1 | 7/2003 | |
| WO | WO 05/000977 A2 | 1/2005 | |
| WO | WO 08/042631 A1 | 4/2008 | |

OTHER PUBLICATIONS

Leach, et al., "The Printing Ink Manual" 5th Edition, Blueprint, New York, p. 194(1993).
Richard J. Lewis, Sr., Hawley's Condensed Chemical Dictionary, 12th Ed., John Wiley & Sons, Inc., New York, p. 1108 (1993).
All Office Actions, U.S. Appl. No. 12/372,957.
All Office Actions, U.S. Appl. No. 13/476,078.
All Office Actions, U.S. Appl. No. 14/164,357.
All Office Actions, U.S. Appl. No. 15/008,548.

\* cited by examiner

SUBSTRATES HAVING IMPROVED CROCKFASTNESS

FIELD OF THE INVENTION

The present invention relates to the printing of substrates with an ink composition comprising a water-based ink. Specifically, the present invention relates to printed substrates webs that are printed with a water-based ink resulting in improved crockfastness.

BACKGROUND OF THE INVENTION

The printing of substrates, such as woven and nonwoven fabrics and films, is well known. The printing of fabrics with inks and dyes is a common and widely used method for imparting patterns and colors to a basic fabric. Many current products, such as diapers and training pants, include printed designs to improve their appearance. A problem with such printed products is that the printed design can be smeared or even removed during the handling of products during manufacturing, packaging, and use.

Pigmented inks are beneficial for use on substrates because they tend to be more resistant to leaching and mechanical rubbing than dye-based inks and thus tend to be more resistant to being removed from the surface of substrates. Pigment-based inks also have better optical density per unit weight (better "mileage") than dye-based inks, meaning that less pigment-based ink is required to create the intensity of color. However, adhesive components are necessary to use along with pigmented inks to prevent removal of the pigment from the surface by mechanical abrasion or chemical leaching.

The industrial importance of pigment-based inks has increased in recent times. This is driven, in part, by the development of many new synthetic substrates that are incapable of being printed with conventional solvent-based or water-based inks, and consumers' preferences that their goods be printed with brand identifiers, aesthetically pleasing designs or functional markings. In order to adapt pigment-based inks for use in a variety of applications, namely low surface tension substrates, others have employed high loads of volatile organic compounds ("VOC's"), thereby reducing the static and dynamic surface tension of the inks. However, volatile organic compounds such as alcohols, esters, ketones, aromatics and aliphatics create environmental hazards in their production, disposal and use. They are also expensive. One example of an ink used on an a low surface tension substrate is set forth in U.S. Pat. No. 5,458, 590 to Schleinz et al., which employs a solvent blend to impart the desired surface tension to the ink.

It has also been recognized that adding small amounts of wax to a polymer adhesive improves the dry rub properties. This is set forth in U.S. Pat. No. 5,458,590 to Schlienz et al, which shows using 0.5-5.0% wax, and in USPA 2007/0100025A1 to Steiner et al, which shows using 0.1 to 2.0% waxes.

Still others have devised methods to adhere ink to low surface tension substrates, such as surface pre-treatment via corona discharge treatment, plasma treatment or use of a primer, as set forth in USPA 2006/0246263 to Yahiaoui et al.

For an ink to be useful, it needs to be in a medium capable of binding with a substrate, either chemically or physically. Where physical binding is desirable, the ink's medium may have adhesive characteristics, and may be somewhat flexible to withstand distortions of the substrate. The flexibility of an aqueous polymer is typically expressed as its glass transition temperature, or Tg. Lower Tg's generally correlate to greater elongation without fracturing. The elongation property is significant in adhesive and coloring because the flexibility/elongation of a formula's polymer affects rub resistance. Specifically, flexibility and softness associated with lower Tg polymers provide a high degree of grab and tack, which is expressed as a high coefficient of friction (CoF). The higher the CoF, the more likely the polymer is to "grab onto" and be "abraded off by" some other substrate or surface, thereby lowering the composition's dry rub resistance. Thus, in conventional inks, the desirable properties of adhesion and flexibility are at the expense of rub resistance. Alternatively, improving rub resistance conventionally creates adhesion and flexibility problems.

Thus, there remains a need for a substrate having improved crockfastness through the use of a water-based ink which is environmentally friendly. There remains a need for a water-based ink that is useful on a variety of substrates including those with low surface tensions, which has desirable wet and dry rub properties, resulting in improved crockfastness of substrates.

SUMMARY OF THE INVENTION

The present invention relates to an ink-printed substrate comprising a substrate and water-based ink composition printed on the substrate, wherein the ink-printed substrate has an average color density of at least about 0.48 or greater. In some embodiments of the present invention, the substrate may be a non-woven fibrous web. In some embodiments of the present invention, the substrate may have a low surface tension. In some embodiments of the present invention, the water-based ink composition may comprise a low $Tg^\circ$ C. water-based polymer component. In some embodiments of the present invention, the substrate may be corona treated prior to application of the ink composition. In some embodiments of the present invention, an over print varnish may be applied after the ink composition has been applied.

DETAILED DESCRIPTION OF THE INVENTION

The present invention concerns the printing of substrates with an ink composition comprising a water-based ink. Specifically, the substrates are useful in an absorbent article, such as a diaper.

As used herein, the following terms have the following meanings:

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants, adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a top sheet and cover sheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core may be substantially cellulose free. The absorbent core does not include an acquisition system, a top sheet, or a back sheet of the absorbent article. In a certain embodiment, the absorbent core would consist essentially of the one or more substrates, the absorbent polymer material, the thermoplastic composition, and optionally the cover layer.

"Airfelt" is used herein to refer to comminuted wood pulp, which is a form of cellulosic fiber.

"Colorant" includes one or more of pigments and or dyes; colorant may further include an acrylic colloidal dispersion, acrylic solution, or surfactants and water.

"Color density" and "Optical Density" refer to a unitless value which refers to the vibrancy of the ink printed unto a substrate. Data derived herein is based on a Gretag/Macbeth SpectroEye spectrophotometer/Densitometer for measurements.

"Color transfer" refers to how much ink is rubbed off from a given sample. Data derived herein is based on the CIE Color System using a Hunter Color LabscanXE color spectrophotometer to measure the amount of color transferred to another substrate.

"Comprise," "comprising," and "comprises" are open ended terms, each specifies the presence of what follows, e.g., a component, but does not preclude the presence of other features, e.g., elements, steps, components known in the art, or disclosed herein.

"Consisting essentially of" is used herein to limit the scope of subject matter, such as that in a claim, to the specified materials or steps and those that do not materially affect the basic and novel characteristics of the subject matter.

"Crockfastness" and "crockfastness rating" shall refer to rub resistance, expressed on a scale of 0 to 5, with 5 showing no sign of color transfer. Crockfastness data reported herein is determined using a certified AATCC Rotary Vertical Crockmeter, Model M238E, supporting a white cloth substrate and rubbing in a reciprocal back and forth circular motion while applying 7.62 pounds per square inch to a printed substrate. Because of its severity, this test equipment is the generally accepted method for measuring rub resistance in the carpet and textile industries.

"Disposable" is used in its ordinary sense to mean an article that is disposed or discarded after a limited number of usage events over varying lengths of time, for example, less than about 20 events, less than about 10 events, less than about 5 events, or less than about 2 events.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Fiber" and "filament" are used interchangeably.

"Glass Transition Temperature" generally refers to the temperature below which a given polymer is physically similar to glass (particularly a breakable solid), and above which the polymer behaves as a liquid, albeit of high viscosity. Tg is an abbreviation for glass transition temperature, with Tg° C. referring to the glass transition temperature expressed in degrees Celsius. The Glass Transition Temperature is measured using ASTM Method D7028-07.

"Ink" and "composition" are used interchangeably herein; an ink or composition may or may not include a colorant.

A "low surface tension substrate", used herein refers to a substrate for receiving ink which exhibits a low surface tension and is therefore difficult to print with conventional inks or methods. These substrates are typically hydrophobic, apolar and inert. Examples of such substrates include webs of polyolefin polymer nonwoven fibers found in synthetic curtains and vertical blinds, feminine care products, diapers, incontinence pants, training pants and disposable wipes. Other examples are continuous films of extruded polyolefin polymer substrates.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. Nonwovens may include hydroentangled nonwovens. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" or "training pant", as used herein, refer to disposable garments having a waist opening and leg openings designed for infant or adult wearers. A pant may be placed in position on the wearer by inserting the wearer's legs into the leg openings and sliding the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants". Suitable pants are disclosed in U.S. Pat. No. 5,246,433, issued to Hasse, et al. on Sep. 21, 1993; U.S. Pat. No. 5,569,234, issued to Buell et al. on Oct. 29, 1996; U.S. Pat. No. 6,120,487, issued to Ashton on Sep. 19, 2000; U.S. Pat. No. 6,120,489, issued to Johnson on Sep. 19, 2000; U.S. Pat. No. 4,940,464, issued to Van Gompel et al. on Jul. 10, 1990; U.S. Pat. No. 5,092,861, issued to Nomura et al. on Mar. 3, 1992; U.S. Patent Publication No. 2003/0233082 A1, entitled "Highly Flexible And Low Deformation Fastening Device", filed on Jun. 13, 2002; U.S. Pat. No. 5,897,545, issued to Kline et al. on Apr. 27, 1999; U.S. Pat. No. 5,957,908, issued to Kline et al on Sep. 28, 1999.

"Polyurethane dispersion", also known as PUD, is a polyurethane which is dispersed in water. Used herein, PUD refers to a catalyst containing, unblocked, fully reacted polyurethane water dispersion.

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed", as used herein, refers to absorbent particulate polymer material that is arranged across the absorbent particulate polymer material area. Optionally, the absorbent particulate polymer material may be arranged such that the substrate layers do not touch in various zones. In one embodiment, the substrate layers may touch in the peripheral areas outside the absorbent particulate polymer material area. It is important to note that the thermoplastic material used in the present invention does not interrupt the substantially continuously distributed absorbent particulate polymer material. Thus, the substantially continuously distributed absorbent particulate polymer material includes the thermoplastic material.

"Substrate" includes any material that the inks of the present invention can be printed on. Thus, substrates of the present invention include, but are not limited to, nonwovens, films, fibrous polyolefin webs, polyolefin webs, cellulosic webs, elastomeric webs, laminates of one or more of the above or any combination of one or more of the above.

"Synurine" refers to a synthetic urine sample, which is prepared by solubilizing 2.0 g potassium chloride, 2.0 g sodium sulfate, 0.85 g ammonium phosphate monobasic, 0.15 g ammonium phosphate dibasic, 0.25 g calcium chloride dehydrate, and 0.50 g magnesium chloride hexahydrate in 1 liter of distilled water.

"Thickness" and "caliper" are used herein interchangeably.

"Very low Tg ° C." used herein is about −82° C.

"Volatile organic compounds", also known as VOC's, include alcohols, esters, ketones, aromatics and aliphatics.

"Wt %" refers to the percentage weight of a specific component relative to the entire composition.

Absorbent Article

Figure 1:
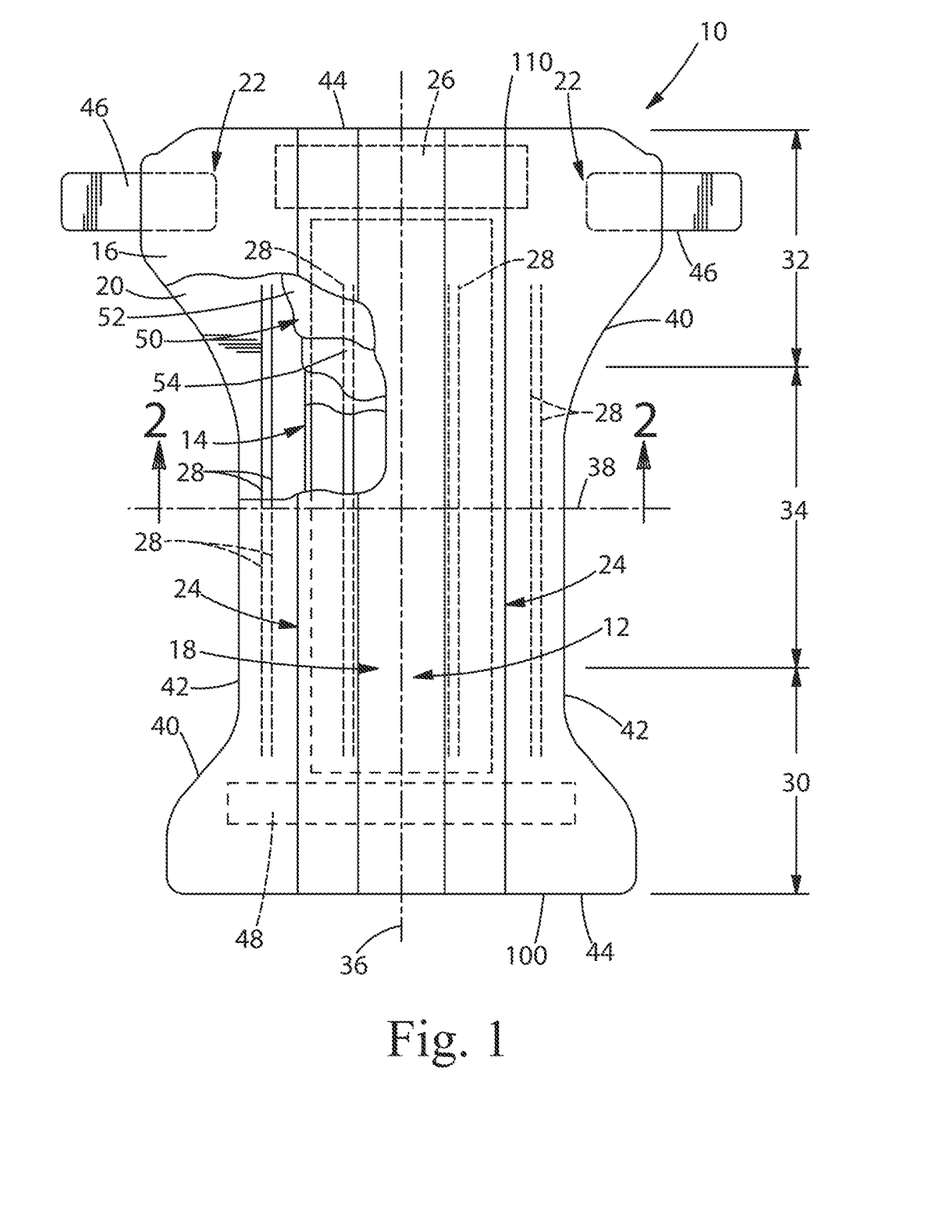
FIG. 1 is a plan view of a diaper in accordance with an embodiment of the present invention.

FIG. 1 is a plan view of a diaper 10 according to a certain embodiment of the present invention. The diaper 10 is shown in its flat out, uncontracted state (i.e., without elastic induced contraction) and portions of the diaper 10 are cut away to more clearly show the underlying structure of the diaper 10. A portion of the diaper 10 that contacts a wearer is facing the viewer in FIG. 1. The diaper 10 generally may comprise a chassis 12 and an absorbent core 14 disposed in the chassis.

The chassis 12 of the diaper 10 in FIG. 1 may comprise the main body of the diaper 10. The chassis 12 may comprise an outer covering 16 including a top sheet 18, which may be liquid pervious, and/or a back sheet 20, which may be liquid impervious. The absorbent core 14 may be encased between the top sheet 18 and the back sheet 20. The chassis 12 may also include side panels 22, elasticized leg cuffs 24, and an elastic waist feature 26.

The leg cuffs 24 and the elastic waist feature 26 may each typically comprise elastic members 28. One end portion of the diaper 10 may be configured as a first waist region 30 of the diaper 10. The first waist region 30 has a first edge 100. An opposite end portion of the diaper 10 may be configured as a second waist region 32 of the diaper 10. The second waist region 32 has a second edge 110. An intermediate portion of the diaper 10 may be configured as a crotch region 34, which extends longitudinally between the first and second waist regions 30 and 32. The waist regions 30 and 32 may include elastic elements such that they gather about the waist of the wearer to provide improved fit and containment (elastic waist feature 26). The crotch region 34 is that portion of the diaper 10 which, when the diaper 10 is worn, is generally positioned between the wearer's legs.

The diaper 10 is depicted in FIG. 1 with its longitudinal axis 36 and its transverse axis 38. The periphery 40 of the diaper 10 is defined by the outer edges of the diaper 10 in which the longitudinal edges 42 run generally parallel to the longitudinal axis 36 of the diaper 10 and the end edges 44 run between the longitudinal edges 42 generally parallel to the transverse axis 38 of the diaper 10. The chassis 12 may also comprise a fastening system, which may include at least one fastening member 46 and at least one stored landing zone 48.

The diaper 20 may also include such other features as are known in the art including front and rear ear panels, waist cap features, elastics and the like to provide better fit, containment and aesthetic characteristics. Such additional features are well known in the art and are e.g., described in U.S. Pat. Nos. 3,860,003 and 5,151,092.

In order to keep the diaper 10 in place about the wearer, at least a portion of the first waist region 30 may be attached by the fastening member 46 to at least a portion of the second waist region 32 to form leg opening(s) and an article waist. When fastened, the fastening system carries a tensile load around the article waist. The fastening system may allow an article user to hold one element of the fastening system, such as the fastening member 46, and connect the first waist region 30 to the second waist region 32 in at least two places. This may be achieved through manipulation of bond strengths between the fastening device elements.

According to certain embodiments, the diaper 10 may be provided with a re-closable fastening system or may alternatively provided in the form of a pant-type diaper. When the absorbent article is a diaper, it may comprise a re-closable fastening system joined to the chassis for securing the diaper to a wearer. When the absorbent article is a pant-type diaper, the article may comprise at least two side panels joined to the chassis and to each other to form a pant. The fastening system and any component thereof may include any material suitable for such a use, including but not limited to plastics, films, foams, nonwoven webs, woven webs, paper, laminates, fiber reinforced plastics and the like, or combinations thereof. In certain embodiments, the materials making up the fastening device may be flexible. The flexibility may allow the fastening system to conform to the shape of the body and thus, reduce the likelihood that the fastening system will irritate or injure the wearer's skin.

For unitary absorbent articles, the chassis 12 and absorbent core 14 may form the main structure of the diaper 10 with other features added to form the composite diaper structure. While the top sheet 18, the back sheet 20, and the absorbent core 14 may be assembled in a variety of well-known configurations, diaper configurations are described generally in U.S. Pat. No. 5,554,145 entitled "Absorbent Article With Multiple Zone Structural Elastic-Like Film Web Extensible Waist Feature" issued to Roe et al. on Sep. 10, 1996; U.S. Pat. No. 5,569,234 entitled "Disposable Pull-On Pant" issued to Buell et al. on Oct. 29, 1996; and U.S. Pat. No. 6,004,306 entitled "Absorbent Article With Multi-Directional Extensible Side Panels" issued to Robles et al. on Dec. 21, 1999.

The top sheet 18 in FIG. 1 may be fully or partially elasticized or may be foreshortened to provide a void space between the top sheet 18 and the absorbent core 14. Exemplary structures including elasticized or foreshortened top sheets are described in more detail in U.S. Pat. No. 5,037,416 entitled "Disposable Absorbent Article Having Elastically Extensible Top sheet" issued to Allen et al. on Aug. 6, 1991; and U.S. Pat. No. 5,269,775 entitled "Trisection Top sheets for Disposable Absorbent Articles and Disposable Absorbent Articles Having Such Trisection Top sheets" issued to Freeland et al. on Dec. 14, 1993.

The back sheet 26 may be joined with the top sheet 18. The back sheet 20 may prevent the exudates absorbed by the absorbent core 14 and contained within the diaper 10 from soiling other external articles that may contact the diaper 10, such as bed sheets and undergarments. In certain embodiments, the back sheet 26 may be substantially impervious to liquids (e.g., urine) and comprise a laminate of a nonwoven and a thin plastic film such as a thermoplastic film having a thickness of about 0.012 mm (0.5 mil) to about 0.051 mm (2.0 mils). Suitable back sheet films include those manufactured by Tredegar Industries Inc. of Terre Haute, Ind. and sold under the trade names X15306, X10962, and X10964. Other suitable back sheet materials may include breathable materials that permit vapors to escape from the diaper 10 while still preventing exudates from passing through the back sheet 10. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont. Other breathable back sheets including nonwoven webs and apertured formed films are described in U.S. Pat. No. 5,571,096 issued to Dobrin et al. on Nov. 5, 1996.

Figure 2:
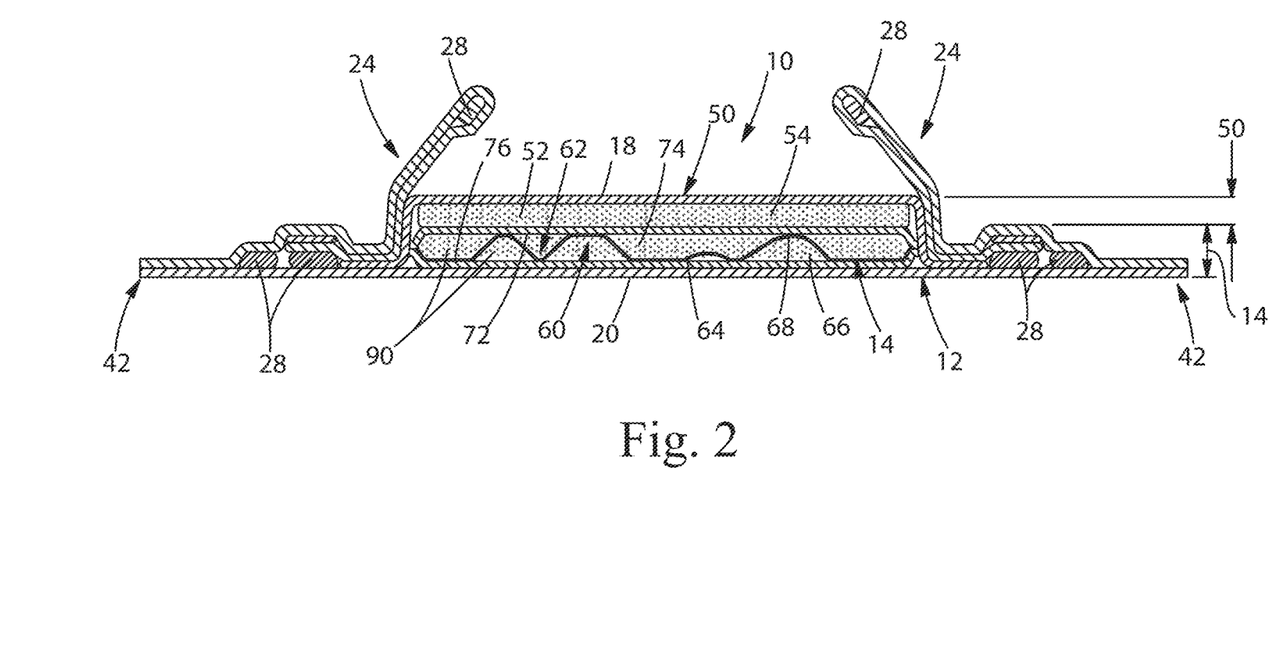
FIG. 2 is a cross sectional view of the diaper shown in FIG. 1 taken along the sectional line 2-2 of FIG. 1.

FIG. 2 shows a cross section of FIG. 1 taken along the sectional line 2-2 of FIG. 1. Starting from the wearer facing side, the diaper 10 may comprise the top sheet 18, the components of the absorbent core 14, and the back sheet 20. According to a certain embodiment, diaper 10 may also comprise an acquisition system 50 disposed between the liquid permeable top sheet 18 and a wearer facing side of the absorbent core 14. The acquisition system 50 may be in direct contact with the absorbent core. The acquisition system 50 may comprise a single layer or multiple layers, such as an upper acquisition layer 52 facing towards the wearer's skin and a lower acquisition 54 layer facing the garment of the wearer. According to a certain embodiment, the acquisition system 50 may function to receive a surge of liquid, such as a gush of urine, and quickly absorb the liquid and distribute it across the absorbent core 14 so that the absorbent core absorbs the liquid before the liquid flows beyond the absorbent layer 14 and out of the diaper 10. In other words, the acquisition system 50 may serve as a temporary reservoir for liquid until the absorbent core 14 can absorb the liquid.

Figure 3:
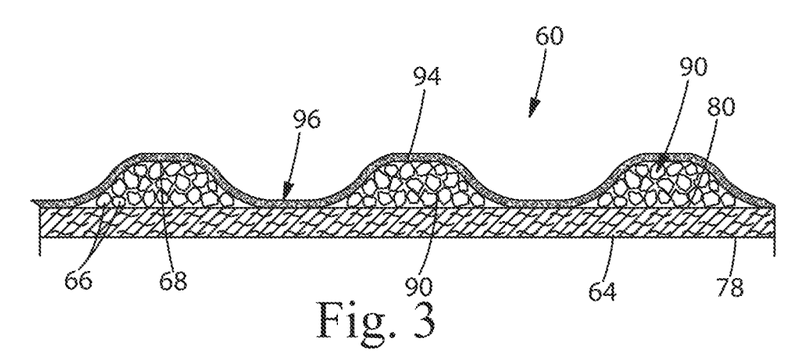
FIG. 3 is a partial cross sectional view of an absorbent core layer in accordance with an embodiment of this invention.

The absorbent core 14 is disposed between the top sheet 18 and the back sheet 20 and comprises two layers, a first absorbent layer 60 and a second absorbent layer 62. As shown in FIG. 3, the first absorbent layer 60 of the absorbent core 14 comprises a substrate 64, an absorbent particular polymer material 66 on the substrate 64, and a thermoplastic composition 68 on the absorbent particulate polymer material 66 and at least portions of the first substrate 64 as an adhesive for covering and immobilizing the absorbent particulate polymer material 66 on the first substrate 64. According to another embodiment, the first absorbent layer 60 of the absorbent core 14 may also include a cover layer on the thermoplastic composition 68.

Likewise, as illustrated in FIG. 2, the second absorbent layer 62 of the absorbent core 14 may also include a substrate 72, an absorbent particulate polymer material 74 on the second substrate 72, and a thermoplastic composition 66 on the absorbent particulate polymer material 74 and at least a portion of the second substrate 72 for immobilizing the absorbent particulate polymer material 74 on the second substrate 72. Although not illustrated, the second absorbent layer 62 may also include a cover layer such as the cover layer.

The substrate 64 of the first absorbent layer 60 may be referred to as a dusting layer and has a first surface 78 which faces the back sheet 20 of the diaper 10 and a second surface 80 which faces the absorbent particulate polymer material 66. Likewise, the substrate 72 of the second absorbent layer 62 may be referred to as a core cover and has a first surface 82 facing the top sheet 18 of the diaper 10 and a second surface 84 facing the absorbent particulate polymer material 74. The first and second substrates 64 and 72 may be adhered to one another with adhesive about the periphery to form an envelope about the absorbent particulate polymer materials 66 and 74 to hold the absorbent particulate polymer material 66 and 74 within the absorbent core 14.

According to a certain embodiment, the substrates 64 and 72 of the first and second absorbent layers 60 and 62 may be a non-woven material. In certain embodiments, the nonwovens are porous and in one embodiment has a pore size of about 32 microns.

Figure 4A:
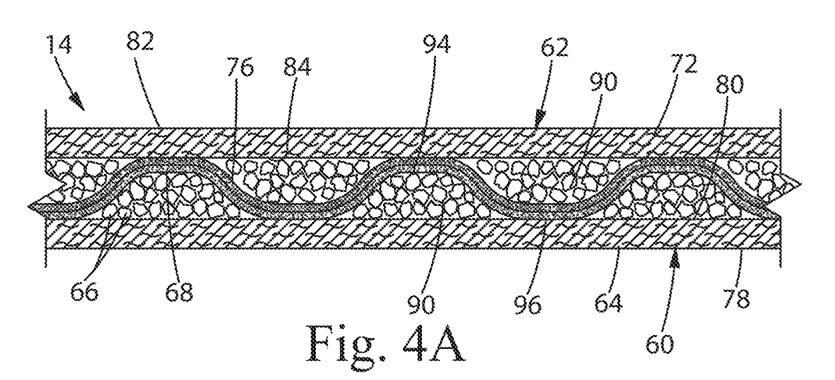
FIG. 4*a* is a partial sectional view of an absorbent core comprising a combination of the first and second absorbent core layers.
Figure 4B:
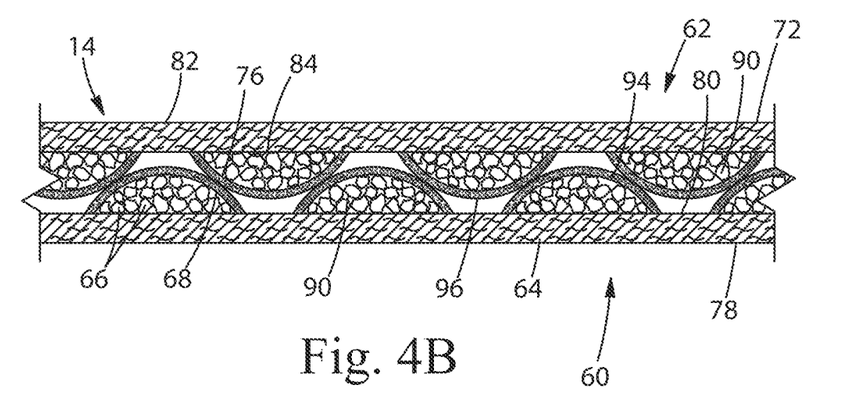
FIG. 4*b* is a partial sectional view of an absorbent core comprising a combination of the first and second absorbent core layers.

As illustrated in FIGS. 3, 4a, and 4b, the absorbent particulate polymer material 66 and 74 is deposited on the respective substrates 64 and 72 of the first and second absorbent layers 60 and 62 in clusters 90 of particles to form a grid pattern comprising land areas 94 and junction areas 96 between the land areas 94. The junction areas 96 in the grid pattern contain little or no absorbent particulate polymer material 66 and 74. The land areas 94 and junction areas 96 can have a variety of shapes including, but not limited to, circular, oval, square, rectangular, triangular, and the like.

The first and second absorbent layers 60 and 62 may be combined together to form the absorbent core 14 such that the grid patterns of the respective first and second absorbent layers 62 and 64 are offset from one another along the length and/or width of the absorbent core 14. The respective grid patterns may be offset such that the absorbent particulate polymer material 66 and 74 is substantially continuously distributed across the absorbent particulate polymer area. In a certain embodiment, absorbent particulate polymer material 66 and 74 is substantially continuously distributed across the absorbent particulate polymer material area despite the individual grid patterns comprising absorbent particulate polymer material 66 and 74 discontinuously distributed across the first and second substrates 64 and 72 in clusters. In a certain embodiment, the grid patterns may be offset such that the land areas 94 of the first absorbent layer 60 face the junction areas 96 of the second absorbent layer 62 and the land areas 94 of the second absorbent layer 62 face the junction areas 96 of the first absorbent layer 60. When the land areas 94 and junction areas 96 are appropriately sized and arranged, the resulting combination of absorbent particulate polymer material 66 and 74 is a substantially continuous layer of absorbent particular polymer material across the absorbent particulate polymer material area of the absorbent core 14. In a certain embodiment, respective grid patterns of the first and second absorbent layer 60 and 62 may be substantially the same.

In a certain embodiment, the amount of absorbent particulate polymer material 66 and 74 may vary along the length of the grid pattern. In a certain embodiment, the grid pattern may be divided into any number of zones, in which the amount of absorbent particulate polymer material 66 and 74 varies from zone to zone. The amount of absorbent particulate polymer material 66 and 74 may, in a certain embodiment, gradually transition from one of the plurality of absorbent zones to another. This gradual transition in amount of absorbent particulate polymer material 66 and 74 may reduce the possibility of cracks forming in the absorbent core 14.

The amount of absorbent particulate polymer material 66 and 74 present in the absorbent core 14 may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. In a particular embodiment, the absorbent core 14 consists essentially of the first and second substrates 64 and 72, the absorbent particulate polymer material 66 and 74, and the thermoplastic adhesive composition 68 and 76. In an embodiment, the absorbent core 14 may be substantially cellulose free.

In certain embodiments which are not substantially cellulose free, the absorbent core 14 can include some amount of cellulose fiber material, such as airfelt. A relatively low amount of cellulosic material is used, in certain embodiments, less than 40 weight percent, or 20 weight percent of cellulosic material, as compared to the weight of absorbent core.

Exemplary absorbent structures for use as the absorbent assemblies are described in U.S. Pat. No. 4,610,678 (Weisman et al.); U.S. Pat. No. 4,834,735 (Alemany et al.); U.S. Pat. No. 4,888,231 (Angstadt); U.S. Pat. No. 5,260,345 (DesMarais et al.); U.S. Pat. No. 5,387,207 (Dyer et al.); U.S. Pat. No. 5,397,316 (LaVon et al.); and U.S. Pat. No. 5,625,222 (DesMarais et al.).

The thermoplastic material 68 and 76 may serve to cover and at least partially immobilize the absorbent particulate polymer material 66 and 74. In one embodiment of the present invention, the thermoplastic material 68 and 76 can be disposed essentially uniformly within the absorbent particulate polymer material 66 and 74. However, in a certain embodiment, the thermoplastic material 68 and 76 may be provided as a fibrous layer which is at least partially in contact with the absorbent particulate polymer material 66 and 74 and partially in contact with the substrate layers 64 and 72 of the first and second absorbent layers 60 and 62. FIGS. 3, 4a, and 4b show such a structure, and in that structure, the absorbent particulate polymer material 66 and 74 is provided as a discontinuous layer, and a layer of fibrous thermoplastic material 68 and 76 is laid down onto the layer of absorbent particulate polymer material 66 and 74, such that the thermoplastic material 68 and 76 is in direct contact with the absorbent particulate polymer material 66 and 74, but also in direct contact with the second surfaces 80 and 84 of the substrates 64 and 72, where the substrates are not covered by the absorbent particulate polymer material 66 and 74. This imparts an essentially three-dimensional structure to the fibrous layer of thermoplastic material 68 and 76, which in itself is essentially a two-dimensional structure of relatively small thickness, as compared to the extension in length and width directions. In other words, the thermoplastic material 68 and 76 undulates between the absorbent particulate polymer material 68 and 76 and the second surfaces of the substrates 64 and 72.

According to certain embodiments, the thermoplastic material 68 and 76 can comprise any thermoplastic material, including, but not limited to adhesive thermoplastic materials, also referred to as hot melt adhesives. Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behavior are herein also understood as thermoplastic materials.

Alternatively, the absorbent core of the present invention may include only one layer. In such an embodiment, the absorbent core includes a first absorbent layer, the first absorbent layer including a first substrate, absorbent particulate polymer material deposited on the first substrate, and thermoplastic material covering the absorbent particulate polymer material on the first substrate, the absorbent particulate polymer material is substantially continuously distributed across the absorbent particulate polymer material area. Alternatively, the first absorbent layer may include a second substrate.

Ink Composition

Embodiments of the present invention include an ink composition comprising a water-based ink. The ink composition may include a very low Tg° C. water-based polymer, a binder component, de-tackifier, resolubility agent, and optionally wax, lubricants and/or pigments. Water-based inks useful in the present invention are available from Environmental Inks and Coatings Corporation, Morganton, N.C., under the following code numbers: EH034677 (yellow); EH057960 (magenta); EH028676 (cyan); EH092391 (black); EH034676 (orange); and EH064447 (green).

The ink composition includes a very low Tg° C. water-based polymer component for providing adhesion to the substrate and improved crockfastness.

In one embodiment, the very low Tg° C. polymer is an acrylic latex. In one embodiment, the very low Tg° C. polymer is from about 5 to about 30 wt % of the ink composition, from about 7 to about 15 wt %, about 11 wt % of the ink composition. Combinations of polymers are also useful in the invention.

While polymers having a very low Tg° C. of about −82° C. are useful in the present invention, polymers having less than about −80 Tg° C., polymers having less than about −75 Tg° C., polymers having less than about −70 Tg° C., polymers having less than about −60 Tg° C., polymers having less than about −50 Tg° C., polymers of less than about −42 Tg° C. would also be suitable. Examples of suitable very low Tg° C. polymers useful in the present invention include acrylics, acrylic latex, styrenated acrylics, ethylene vinyl acetate, ethylene vinyl chlorides and styrene butadiene rubbers (SBR's).

The ink composition may include a binder component. The binder component may be from about 20 to about 45 wt % of the ink composition. In one embodiment of the present invention, the binder component may be a polyurethane dispersion (also known herein as "PUD"). The PUD may be a high elongation, high tensile strength, high hardness, water-based polymeric dispersion.

The ink composition may include a de-tackifier to improve crockfastness. Suitable de-tackifiers include inorganic materials, with talc being useful in one embodiment. Other potential de-tackifiers may include calcium carbonate, silicas and magnesium stearates. The de-tackifier may comprise from about 1 to about 4 wt % of the composition.

The ink may include a wax component. The wax component may be from about 8 to about 18 wt % of the ink composition. A wax or wax blend may be useful in the present invention. Appropriate waxes/blends include polyethylene, carnauba, paraffin, silicone oil, polypropylene, polyolefin blends and combinations thereof.

The ink may include a resolubility agent. The resolubility agent may be from about 5.0 to about 16.0 wt % of the ink composition. Resolubility agents useful in the present invention include acrylics solutions and dispersions with a high to medium degree of carboxyl functionality. In one embodiment, medium acid number, acrylic colloidal dispersion resolubility agents are useful in the present invention.

The ink may include additional waxes and lubricants for detackification and lowering CoF. The additional wax/lubricant blend may be comprised of carnauba (the wax) and silicone oil (the lubricant). In one embodiment, the wax/lubricant blend is from about 1 to about 4 wt % of the composition. Waxes useful in the present invention include polyethylene, polypropylenes, high density polyethylene, low density polyethylene and paraffin.

Although not necessary, the ink may include pigments. Examples of suitable pigments include, but are not limited to, Blue 15:3, Violet 23, Violet 27, Yellow 14, Yellow 74, Yellow, 83, Yellow 97, Yellow 13, Green 7, Red 2, Red 22, Red 48:1, Red 57:1, Red 122, Red 184, Red 238, Red 269, Red 49:1, Red 81:1 Red 49:2, Red 166, Red 170, Orange 5, Orange 16, Orange 46, White 7, Black 7, iron oxides, and combinations thereof. In one embodiment, from about 10 to about 16 wt % pigments are employed, but this may vary according to the specific color and desired density. In one embodiment, pigments in a colloidal dispersion, collectively a colorant, are useful in the present invention.

The ink composition may include surfactants. Surfactants may be present in the range of from about 1.0 to about 10.0 wt % of the ink composition. Surfactants useful in the present invention include dioctyl sulfosuccinates, phosphate esters, alkoxylated alcohols, ethoxylated diols, and mixtures or blends thereof.

In one embodiment of the present invention, an over print varnish (also known herein as "OPV") may be used. An overprint varnish useful in the present invention is available as code number EH012608 from Environmental Inks and Coatings Corporation, or Morganton, N.C. The overprint varnish may comprise a very low Tg° C. polymer as described above, polyurethane dispersion as described above, a colloidal dispersion as described above, a surfactant as described above, talc as described above, ammonia, and water. The very low Tg° C. polymer may be present in the OPV in an amount of from about 3% to about 20%, from about 5% to about 15%. The polyurethane dispersion may be present in the OPV in an amount of from about 30% to about 60%. The colloidal dispersion may be present in the OPV in an amount of from about 5% to about 25%. The surfactant may be present in the OPV in an amount of from about 1% to about 15%. Talc may be present in the OPV in an amount of from about 0.1% to about 10%. Ammonia may be present in the OPV in an amount of from about 0.1% to about 10%. Water may be present in the OPV in an amount of from about 1% to about 50%. Any other component described in the ink composition may also be useful in the OPV.

The ink composition may be applied to the substrate by any method known in the art. Specifically, the ink composition may be applied to the substrate using ink jet printers, flexographic printing presses, gravure printing presses, or a combination thereof. The ink composition may be printed on a number of article components including, but not limited to, the backsheet, topsheet, cuffs, etc. In one embodiment, the ink composition is applied to the substrate by flexographic or rotogravure printing. A metering roll or doctor blade system may be used. In one embodiment, printing is performed in excess of 500 ft/min, requiring only minimal adjustment in pH.

The OPV may be applied to the printed substrate by any method known in the art. The OPV may be applied to the entire substrate, to only the ink-printed area, or to any combination thereof. The OPV may be applied to the substrate using ink jet printers, flexographic printing presses, gravure printing presses, or a combination thereof. In one embodiment, the OPV is applied to the printed substrate by flexographic or rotogravure printing. In one embodiment, the OPV is printed using an 80-100% screen printing plate. The OPV may be printed after the inks are printed and allowed to dry by an inline forced air dryer. The dryer temperature for drying the inks and the OPV may be from about 80° C. to about 95° C. The OPV may be printed on a number of article components including, but not limited to, the backsheet, topsheet, cuffs, etc. A metering roll or doctor blade system may be used. In one embodiment, printing is performed in excess of 500 ft/min, requiring only minimal adjustment in pH.

Untreated polyolefin films and nonwoven substrates have low surface energies. Untreated polypropylene and polyethylene substrates at 20° C. will have low surface energies (usually 30 to 32 dynes/cm). Water at 20° C. has a surface tension of 72.8 dynes/cm compared to 22.3 for ethyl alcohol which is often the solvent used in solvent-based inks. As a result, water-based inks may not adhere or print well on polyolefin fibrous nonwoven substrates and films. In one embodiment, water-based ink systems may require a substrate surface tension of from about 40 to about 45 dynes/cm in order to provide acceptable adhesion and wetout. Also, the addition of surfactants to lower the surface tension of the water-based ink or lacquer composition may be useful. However, the addition of surfactants may cause foaming. Therefore, in one embodiment, the polyolefin substrates may require some amount of surface treatment in order to accept a water-based ink. In one embodiment, the surface energy of the substrate may be from about 3 dynes/cm to about 10 dynes/cm greater than the surface tension of the ink; the surface energy of the substrate may be from about 7 dynes/cm to about 9 dynes/cm greater than the surface tension of the ink.

Any surface treatment known in the art to may be used in the present invention. Surface treatments include, but are not limited to, plasma treatment, UV treatment, flame treatment, heat treatment, abrasion treatment, and corona treatment.

In one embodiment, prior to printing the ink composition on the substrate, the substrate may be corona treated. Corona treatment is a method of increasing surface energy on substrates to promote surface wetting of and adhesion to the substrate when printing, coating or laminating. The purpose of corona treatment is to increase the surface energy of the substrate web to improve the wettability and adhesion characteristics of inks and adhesives to polyolefin films and nonwoven substrates. Unlike the purely mechanical bond, (as in the case of an ink penetrating into a porous surface like paper), plastic films and nonwoven substrates may need some means of surface treatment to achieve acceptable chemical bonding with the ink or adhesive.

Corona treatment systems are made of several components designed to apply a high voltage, high frequency electrical discharge to the substrate. Corona discharge introduces polar groups into the polymeric surfaces and, as a consequence, increases its surface energy, wettability, and adhesion characteristics. The main chemical mechanism of corona treatment is oxidation. The high voltage ionizes the air in the air gap creating a corona, which modifies the surface and increases the surface energy of the substrate passing over the electrically grounded roll. The effect is not long lasting and the increase in the surface energy dissipates within two to six weeks. Use of corona treatment may raise the surface energy level to value levels of from about 38 to about 44 dynes/cm, or from about 40 to about 42 dynes/cm, depending on the Watt density of the corona treatment. Corona treatments may be applied at from about 1.0 to about 10.0 watts per square feet per minute; from about 3.0 to about 5.0 watts per square feet per minute; or about 4.0 watts per square feet per minute.

Thus, in some embodiments of the present invention, by utilizing surface treatments known in the art, including corona treatment mechanisms, the surface energy of substrates may be increased, thereby improving crockfastness. As shown in the data below, corona treatment may be especially valuable when considering baby oil rub-off resistance.

Test Measurement Methods
Crockfastness Measurement Method

The purpose of the crockfastness method is to measure the amount of color transferred from the surface of a printed surface to the surface of a standard woven swatch, by rubbing using a rotary vertical crockmeter. Color transfer (crocking) is quantified using a tristimulus color meter (spectrophotomer/colorimeter) and converted to a crock value scale that ranges from 0=extensive transfer to 5=no transfer of color.

This method is applicable to ink printed nonwovens. Crocking can be performed on a dry basis or by wetting the standard woven swatch with water, saline, apple juice, or baby oil. The crocking area should be an area that is substantially covered with ink.

References: AATCC Test Method 116-2005, Colorfastness to Crocking: Rotary Vertical Crockmeter Method
Equipment:
Rotary vertical crockmeter: AATCC Crockmeter, Model CM6; available from Textile Innovators Corporation, Windsor N.C.
Crockmeter cloth: 2 in. by 2 in. square woven swatch; available from Testfabrics Inc., West Pittston Pa.

Tristimulus color meter (spectrophotomer/colorimeter): HunterLab Labscan XE with Universal Software 3.80; available from Hunter Associates Laboratory Inc., Reston Va., or equivalent
Analytical balance: Top loading, accurate to ±0.001 g; convenient source
Weighing boats: 3 in. square, disposable polyethylene; convenient source
Volumetric flask: 100 mL, Class A; convenient source
Reagents:
Purified water Distilled, deionized, or reverse osmotic purified; convenient source
Sodium chloride, ACS reagent grade, convenient source
0.9% saline solution prepared by adding 0.908 g±0.001 g of sodium chloride to 100 mL of purified water
Apple juice, Gerber Baby's $1^{st}$ Foods® apple juice from concentrate
Baby oil, Johnson & Johnson's "Johnson Baby Oil® regular unscented baby oil.
Instrument Set-Up and Calibration:

The Hunter Color meter (spectrophotomer/colorimeter) settings are as follows:
Geometry 45/0
Color Scale CIE L*a*b*
Illumination: D65
View Angle 10°
Port Size 0.7"
Illumination Area 0.5"
Color is reported as L* a* b* values±0.01 units
Calibrate the instrument per the vendor instructions using the standard black and white plates provided by the vendor. Calibration should be performed each day before analyses are performed.
The analyses should be performed in a temperature and humidity controlled laboratory (23° C.±2° C. and 50%±2% relative humidity, respectively).

Procedure:
1. All samples and crockmeter cloths are equilibrated at 23° C.±2° C. and 50%±2% relative humidity for at least 2 hours before analysis.
2. Center a single crockmeter cloth over the port of the color meter (spectrophotomer/colorimeter) and cover it with the standard white plate. Take and record the reading. Remove the crockmeter cloth from the instrument and place it into a weighing boat with the side just measured (hereafter referred to as Side A) facing upward.
   Note: It is important to maintain the orientation of the crockmeter cloth throughout the experiment, such that all color measurements and the rubbing are performed on the same side.
3. Using tweezers, remove the crockmeter cloth from the weighing boat. Place the weighing boat on the analytical balance and tare the weight.
4. Place the crockmeter cloth, Side A up, into the weighing boat and record its mass to 0.001 g. Calculate 65% of the mass of the crockmeter cloth to 0.001 g and record as M1.
5. Using a disposable pipette, add an amount of the test solution equivalent to M1 (±5%) to the surface of the crockmeter cloth, uniformly wetting it.
6. Immediately remove the wetted crockmeter cloth from the weighing dish and secure it to the testing foot of the crockmeter with Side A facing toward the sample surface.

Note: The wetted crockmeter cloth should be handled carefully and quickly after it is wetted to prevent loss of moisture before the sample is rubbed.
7. Place the sample under the crockmeter foot, such that the region to be tested is substantially covered with ink and is directly under, and facing the foot.
8. Lower the foot onto the sample. Securely hold the sample in place and turn the crockmeter handle five full rotations.
9. Raise the foot and remove the crockmeter cloth. Place it into the weighing boat with Side A facing upward. Holding the crockmeter cloth at its edges, gently smooth its surface.
10. Allow the cloths to dry completely (the baby oil will not dry completely, allow it to dry for at least 8 hours).
11. Take the crockmeter cloth and place Side A facing the orifice of the color meter (spectrophotomer/colorimeter), being careful to center the rubbed region over the port. Cover it with the standard white plate. Take and record the reading.
12. Repeat steps 2 through 11 for each replicate and each requested test solution.
   Note: At least 5 replicates are analyzed using only the 0.9% saline test solution for each color. The submitter may request more replicates and/or different test solutions.

Calculations:
Calculate $\Delta E^*$ as follows from the set of color reading on the untreated crockmeter cloth (blank) and the same cloth after crocking (rubbed):

$$\Delta E^* = [(L^*_{blank} - L^*_{rubbed})^2 (a^*_{blank} - a^*_{rubbed})^2 (b^*_{blank} - b^*_{rubbed})^2]^{1/2}$$

If $\Delta E^*$ is greater than or equal to 12, the crocking value is calculated as:

$$\text{Crocking Value} = 5.063244^{(-0.059532 \times \Delta E^*)}$$

If $\Delta E^*$ is less than 12, the crocking value is calculated as:

$$\text{Crocking Value} = 4.0561216^{(-0.041218 \times \Delta E^*)}$$

Reporting:
Crocking Values are reported as the average of 5 replicates to ±0.1 units.

Optical Density/Color Density Measurement Method

The purpose of this method is to provide a procedure for quantitatively measuring color and density (ink intensity) of colored (printed and pigmented) materials with a convenient and portable device, the GreytagMacbeth SpectroEye. In this method, the reflective color and density of a material is measured with a Hand Held Spectrophotometer using standardized procedures and reference materials.

Density is a unitless value. Density is a function of the percentage of light reflected. Density=$\log_{10}$ 1/R, where R=Reflectance. The table below shows the relationship of percent reflectance to Density.

| % Reflectance | Density |
|---|---|
| 100% | 0.0 D |
| 10% | 1.0 D |
| 1% | 2.0 D |
| 0.1% | 3.0 D |
| 0.01% | 4.0 D |

Figure 5:
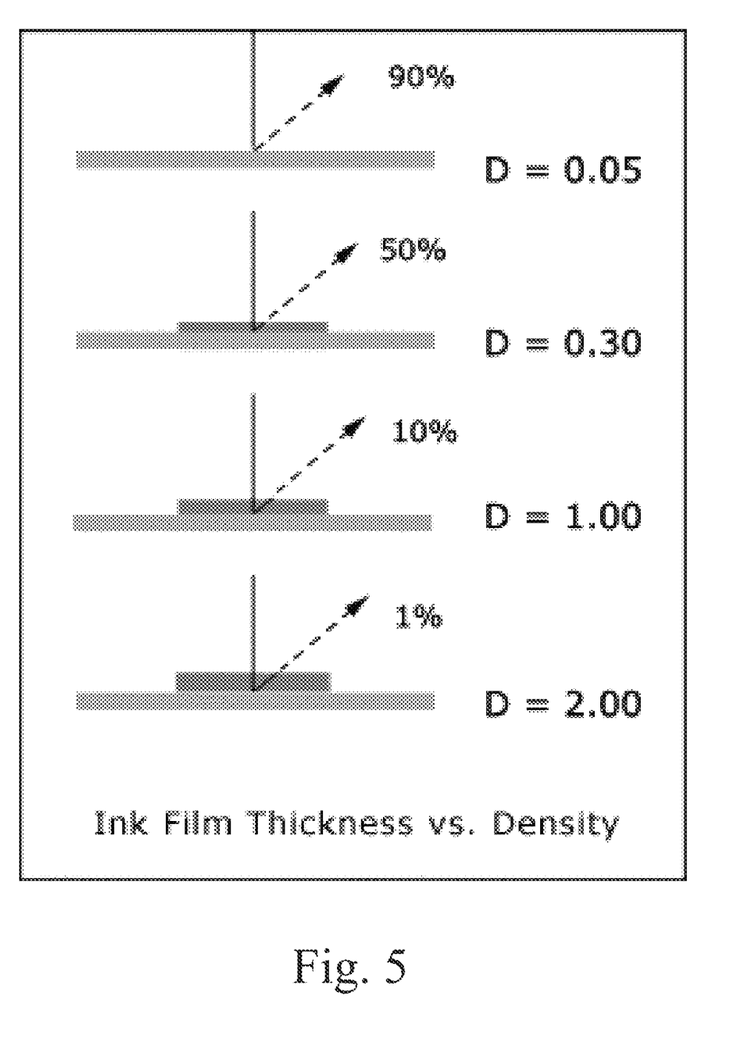
FIG. 5 is a graph of ink film thickness versus density of various ink printed substrates of the present disclosure.

0-100% solid patches of each ink printed are measured, and the density values recorded and compared to the relative specifications. This will indicate to the press operator whether the amount of ink should be increased or decreased. As FIG. 5 indicates, ink film thickness is approximately proportional to optical density.

A printing press naturally varies, and a typical tight tolerance for density is ±0.05 D. A good demonstration of the normal variation of the press is to measure the same patch on ten press samples, pulled at one-minute intervals, and record and plot the density values. This shows how density varies with no adjustments to the press.

This method is applicable to materials such as films, nonwovens, and composite structures (laminates) that have been colored via printing, tinting, or pigmentation.

This method is applicable to measurements taken by the GretagMacbeth SpectroEye spectrodensitometer. Data generated by any other portable spectrophotometers, spectrodensitometers, colorimeters, densitometers are not guaranteed by this method.

Equipment:
Hand Held Spectrophotometer: 45°/0° configuration, hemispherical geometry, GreytagMacbeth SpectroEye.
Scissors: Convenient type
Tissue: Convenient type, without embossing, lotion or brighteners, (e.g. Kimwipes)
White Standard Board: PG2000 Provided by Sun Chemical-Vivitek Division, 1701 Westinghouse Blvd., Charlotte, N.C. 28273, Phone: (704)-587-8381
Facilities: The samples and instrument should be kept in an area free of high humidity (75° F. & 50% relative humidity ideally) and corrosive vapors, and the samples should be protected from contamination by dirt or lint.
Set up the color meter as follows:
   Physical Filter: None
   White Base: Abs
   Observer: 2°
   Density Standard: ANSI T
   Illumination: C
NOTE: Ensure that the spectrophotometer is set to read L* a* b* units and not Hunter Lab units Procedure:
1. Select a sample region for analysis. For printed film and nonwovens carefully place 1 ply of the 100% coverage area sample over the PG2000 white standard board.
2. Place the Macbeth SpectorEye aperture over the sample and confirm that only sample material can be viewed within the instruments aperture window.
3. Toggle through the measurement menu to Read and Record the color (L*, a*, and b*) and Density values for each sample.

Calculations:
1. For each ink, measure and record density readings.
2. For each measurement set, use at least three recordings to calculate and report the average and a standard deviation.

Reporting: Density values are to be reported to the nearest 0.01 units

Leachability Measurement Method

Equipment:
Tristimulus color meter (spectrophotomer/colorimeter): HunterLab Labscan XE with Universal Software 3.80; available from Hunter Associates Laboratory Inc., Reston Va., or equivalent Glass Liquid Cup Assembly (Part LSXE-SC-ASSY, HunterLab) consisting of a port insert, 2.5" glass cup, black spacer ring, white ceramic disk, and opaque cover
Orbital rocker: convenient source
25 mL glass screw top vials
Leachability is tested in 0.9% w/w saline, 100% isopropanol, clear baby oil
Instrument Set-up and Calibration:

The Hunter Color meter (spectrophotomer/colorimeter) settings are as follows:
Geometry 45/0
Color Scale CIE L*a*b*
Illumination: D65
View Angle 2°
Port Size 1.75"
Illumination Area 1.0"
Calibrate the instrument per the vendor instructions using the standard black and white plates provided by the vendor. Calibration should be performed each day before analyses are performed.

Extraction:
1. Cut three 6 by 6 cm squares of the printed material.
2. Fold all three squares and place into a 25 mL vial, add 15 mL of test solution, seal and shake vigorously until the specimens are wetted and submerged into the test solution.
3. Extract the sample at 37° C. (±2° C.) for 12 hours with moderate mixing on the orbital rocker.
4. A blank test solution, with no printed specimen, is treated in the same fashion for comparison.

Measurement:
1. Insert the spacer ring into the sample cup.
2. Fill the cup with the extract (or blank) such that the liquid is just above the top of the spacer ring.
3. Place the ceramic disk on top of the spacer ring and set the assembled sample cup on top of the sample insert.
4. Cover the sample cup with the opaque cover.
5. Take reading for L* a* b* values and record to ±0.01 units
6. Repeat for the blank test solution.

Calculation:

$$\Delta E^* = [(L^*_{blank} - L^*_{extract})^2 (a^*_{blank} - a^*_{extract})^2 (b^*_{blank} - b^*_{extract})^2]^{1/2}$$

Leachability Colorfastness Rating = $5.0 + 0.0045 (\Delta E^*)^2 - 0.2553(\Delta E^*)$ Leachability Colorfastness Rating should be reported as the average of a minimum of 3 replicates to ±0.01 units.

Data and Analysis

Crockfastness and color density data generated relative to the ink compositions of the present invention is as follows:

| Ink | INK ONLY PRINTED NONWOVEN | | | | | | | | | | | |
|---|---|---|---|---|---|---|---|---|---|---|---|---|
| | Dry CFR | | Synurine CFR | | Water CFR | | Apple Juice CFR | | Baby Oil CFR | | Density | |
| Color | Xbar | Sigma | Xbar | Sigma | Xbar | Sigma | Xbar | Sigma | Xbar | Sigma | Xbar | Sigma |
| Yellow | 3.0 | 0.1 | 4.1 | 0.2 | 4.3 | 0.1 | 4.3 | 0.1 | 3.1 | 0.2 | 0.53 | 0.02 |
| Magenta | 3.4 | 0.1 | 3.9 | 0.1 | 3.9 | 0.2 | 4.0 | 0.1 | 2.8 | 0.1 | 0.49 | 0.04 |
| Cyan | 3.8 | 0.1 | 4.4 | 0.1 | 4.5 | 0.1 | 4.2 | 0.1 | 3.1 | 0.1 | 0.56 | 0.03 |
| Black | 4.0 | 0.1 | 4.5 | 0.2 | 4.4 | 0.1 | 4.6 | 0.1 | 3.1 | 0.1 | 0.56 | 0.05 |

| Ink | INK + OPV (NO CORONA) PRINTED NONWOVEN | | | | | | | | | | | |
|---|---|---|---|---|---|---|---|---|---|---|---|---|
| | Dry CFR | | Synurine CFR | | Water CFR | | Apple Juice CFR | | Baby Oil CFR | | Density | |
| Color | Xbar | Sigma | Xbar | Sigma | Xbar | Sigma | Xbar | Sigma | Xbar | Sigma | Xbar | Sigma |
| Yellow | 4.0 | 0.1 | 4.4 | 0.1 | 4.5 | 0.1 | 4.4 | 0.1 | 3.4 | 0.1 | 0.52 | 0.05 |
| Magenta | 4.3 | 0.1 | 4.4 | 0.1 | 4.6 | 0.1 | 4.4 | 0.1 | 3.9 | 0.1 | 0.49 | 0.02 |
| Cyan | 4.6 | 0.1 | 4.8 | 0.1 | 4.9 | 0.1 | 4.4 | 0.1 | 4.0 | 0.1 | 0.56 | 0.03 |
| Black | 4.6 | 0.1 | 4.8 | 0.1 | 4.8 | 0.1 | 4.7 | 0.1 | 4.0 | 0.1 | 0.56 | 0.04 |

| Ink | INK + CORONA (NO OPV) PRINTED NONWOVEN | | | | | | | | | | | |
|---|---|---|---|---|---|---|---|---|---|---|---|---|
| | Dry CFR | | Synurine CFR | | Water CFR | | Apple Juice CFR | | Baby Oil CFR | | Density | |
| Color | Xbar | Sigma | Xbar | Sigma | Xbar | Sigma | Xbar | Sigma | Xbar | Sigma | Xbar | Sigma |
| Yellow | 2.6 | 0.2 | 3.3 | 0.4 | 3.2 | 0.4 | 4.3 | 0.1 | 4.1 | 0.1 | 0.50 | 0.02 |
| Magenta | 2.8 | 0.4 | 2.6 | 0.1 | 2.6 | 0.2 | 3.2 | 0.2 | 4.1 | 0.2 | 0.57 | 0.03 |
| Cyan | 3.6 | 0.1 | 3.2 | 0.1 | 3.5 | 0.4 | 3.6 | 0.4 | 4.2 | 0.1 | 0.64 | 0.03 |
| Black | 3.8 | 0.1 | 3.1 | 0.1 | 2.9 | 0.1 | 3.3 | 0.2 | 3.6 | 0.2 | 0.48 | 0.06 |

| INK + CORONA + OPV PRINTED NONWOVEN | | | | | | | | | | | |
|---|---|---|---|---|---|---|---|---|---|---|---|
| Ink | Dry CFR | | Synurine CFR | | Water CFR | | Apple Juice CFR | | Baby Oil CFR | | Density | |
| Color | Xbar | Sigma | Xbar | Sigma | Xbar | Sigma | Xbar | Sigma | Xbar | Sigma | Xbar | Sigma |
| Yellow | 4.2 | 0.2 | 3.5 | 0.2 | 3.8 | 0.2 | 4.0 | 0.2 | 4.2 | 0.2 | 0.58 | 0.06 |
| Magenta | 3.7 | 0.3 | 3.3 | 0.3 | 3.2 | 0.2 | 3.6 | 0.2 | 4.0 | 0.2 | 0.62 | 0.02 |
| Cyan | 4.0 | 0.3 | 3.3 | 0.1 | 3.4 | 0.5 | 3.6 | 0.1 | 3.9 | 0.1 | 0.71 | 0.05 |
| Black | 4.2 | 0.1 | 3.6 | 0.2 | 3.4 | 0.1 | 3.9 | 0.1 | 3.6 | 0.1 | 0.57 | 0.02 |

As shown by the data above, the ink compositions of the present invention are useful in improving crockfastness. Specifically, the crockfastness values of the present invention are greater than about 2.5, greater than about 3.0, greater than about 3.1, greater than about 3.2, greater than about 3.3, greater than about 3.4, greater than about 3.5, greater than about 3.6, greater than about 3.7, greater than about 3.8, greater than about 3.9, greater than about 4.0, greater than about 4.1, greater than about 4.2, greater than about 4.3, greater than about 4.4, greater than about 4.5, greater than about 4.6, greater than about 4.7, greater than about 4.8.

Also, as shown by the data above, the ink compositions of the present invention are useful in improving color density. Specifically, the color density values of the present invention are greater than about 0.40, greater than about 0.45, greater than about 0.48, greater than about 0.50, greater than about 0.52, greater than about 0.55, greater than about 0.57, greater than about 0.60, greater than about 0.62, greater than about 0.64, greater than about 0.68, greater than about 0.70.

Typically, screen values, also known as % dot coverage, impact the crockfastness rating and color density of the printed image on the substrate. Generally, the higher the % screen value, the lower the crockfastness rating. Conversely, the higher the % screen value, the higher the optical density, as the thickness of the printed ink thickens. Eventually, however, the density values may plateau. Inks of the present invention may be printed at slightly greater than 0% screen values (clear/white), up to 100% screen value (maximum color), or at any % screen value in between.

Typically, improved color density for a given ink results in a reduction in the ink adhesion and crockfastness of the ink. The rate of loss of crockfastness versus the increase in optical density is defined as the Crockfastness-Loss-to-Density-Ratio (CLDR). CLDR is a non-linear relationship that is further quantified by the following equation for dry and hydrophilic wetting agents: $CLDR = \delta Y/\delta X = -(4.46X + 0.73)$, wherein X is the color density and Y is the crockfastness.

For baby oil wetted printed nonwovens, $CLDR = \delta Y/\delta X = -1.61$, wherein X is the color density and Y is the crockfastness.

The present invention is directed to minimizing the CLDR to improve ink adhesion.

Oftentimes, the CLDR of inks has a value of less than about −0.6.0. In some embodiments of the present invention, the CLDR has a negative value of from about −1.0 to about −6.0; from about −1.0 to about −3.0; from about −2.0 to about −3.0.

In one embodiment, the baby oil crockfastness for inks in the present invention are less sensitive to increases in the optical density. This is a desirable characteristic given the broad, frequent, and acceptable use of baby oil by caregivers to treat the skin of babies and the need for improved baby oil resistance of the ink printed images. In some embodiments of the present invention, the CLDR relative to baby oil has a value of from about −1.0 to about −3.0; from about −1.0 to about −2.0.

Oftentimes, pigments tend to solubilize when exposed to certain chemical substances. This is known as "leachability" and may also be referred to as "pigment bleed." In diaper usage, many current printing inks may react with or be leached by common fluids such as water, saline solution, baby oil, etc. that may come into contact with a baby's skin. These fluids may cause the ink-printed image to rub off, smear, transfer to the skin, transfer to furniture and/or other surfaces. In one embodiment of the present invention, once the ink composition has been printed and dried onto the substrate, leachability improves. As the data below indicate, in one embodiment of the present invention, Cyan and Black exhibit no visible pigment leaching by any of the chosen solutions. Thus, in one embodiment of the present invention, the leachability of the ink composition is less than about 10, less than about 5, about 0.

| Leachability Results (ΔE Color Change of Fluid) | | | | | |
|---|---|---|---|---|---|
| | Water | | Saline Solution | | Baby Oil | |
| Ink Colors | Ink Only | Ink + OPV | Ink Only | Ink + OPV | Ink Only | Ink + OPV |
| Yellow | 0.0 | 0.0 | 0.0 | 0.0 | 9.4 | 7.4 |
| Magenta | 0.0 | 0.0 | 4.4 | 3.2 | 0.0 | 0.0 |
| Cyan | 0.0 | 0.0 | 0.0 | 0.0 | 0.0 | 0.0 |
| Black | 0.0 | 0.0 | 0.0 | 0.0 | 0.0 | 0.0 |

| Colorfastness Results | | | | | |
|---|---|---|---|---|---|
| | Water | | Saline Solution | | Baby Oil | |
| Ink Colors | Ink Only | Ink + OPV | Ink Only | Ink + OPV | Ink Only | Ink + OPV |
| Yellow | 5.0 | 5.0 | 5.0 | 5.0 | 3.0 | 3.4 |
| Magenta | 5.0 | 5.0 | 4.0 | 4.2 | 5.0 | 5.0 |
| Cyan | 5.0 | 5.0 | 5.0 | 5.0 | 5.0 | 5.0 |
| Black | 5.0 | 5.0 | 5.0 | 5.0 | 5.0 | 5.0 |

All documents cited in the Detailed Description of the invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

While particular embodiments of the present invention have been illustrated and described, it would be obvious to those skilled in the art that various other changes and modifications can be made without departing from the spirit and the scope of the invention. It is therefore intended to cover in the appended claims all such changes and modifications that are within the scope of this invention.

What is claimed is:

1. An ink-printed substrate, comprising:
   a. a water-based ink composition printed on a substrate, forming a water-based ink printed area;
   b. an overprint varnish comprising between about 30% and about 60% of a polyurethane dispersion by weight of the overprint varnish, between about 3% and about 20% of a very low $Tg°$ C. water-based polymer by weight of the overprint varnish, and between about 1% and about 15% of a surfactant by weight of the overprint varnish;
   wherein the ink-printed substrate comprises a Crockfastness-Loss-to-Density Ratio of about −1.0 to about −6.0.

2. The ink-printed substrate of claim 1, wherein the substrate comprises one of a non-woven, a film, a polyolefin web, a fibrous polyolefin web, a cellulosic web, an elastomeric web or combinations thereof.

3. The ink-printed substrate of claim 1, wherein the substrate exhibits a low surface tension.

4. The ink-printed substrate of claim 1, wherein the substrate is at least one of hydrophobic, apolar, or inert.

5. The ink-printed substrate of claim 1, wherein the water-based ink composition comprises a very low $Tg°$ C. water-based polymer component.

6. The ink-printed substrate of claim 1, wherein the water-based ink composition comprises a binder.

7. The ink-printed substrate of claim 1, wherein the overprint varnish is applied to the water-based ink printed area.

8. The ink-printed substrate of claim 1, wherein the ink-printed substrate has an average crockfastness of at least about 3 or greater, according to the Crockfastness Measurement Method.

9. A disposable absorbent article, comprising: a topsheet, a backsheet, and an absorbent core between the topsheet and the backsheet, the backsheet comprising the ink-printed substrate of claim 1.

10. An ink-printed substrate, comprising:
    a. a substrate pretreated with a corona treatment;
    b. a water-based ink composition printed on the substrate, forming a water-based ink printed area;
    c. an average crockfastness of at least about 2.5 or greater, according to the Crockfastness Measurement Method; and
    d. an overprint varnish comprising between about 30% and about 60% of a polyurethane dispersion by weight of the overprint varnish, between about 3% and about 20% of a very low $Tg°$ C. water-based polymer by weight of the overprint varnish, and between about 1% and about 15% of a surfactant by weight of the overprint varnish;
    wherein the ink-printed substrate comprises a Crockfastness-Loss-to-Density Ratio of about −1.0 to about −6.0.

11. The ink-printed substrate of claim 10, wherein the substrate comprises one of a non-woven, a film, a polyolefin web, a fibrous polyolefin web, a cellulosic web, an elastomeric web or combinations thereof.

12. The ink-printed substrate of claim 10, wherein the substrate has a low surface tension.

13. The ink-printed substrate of claim 10, wherein the substrate is at least one of hydrophobic, apolar, or inert.

14. The ink-printed substrate of claim 10, wherein the water-based ink composition comprises a very low $Tg°$ C. water-based polymer component.

15. A disposable absorbent article, comprising: a topsheet, a backsheet, and an absorbent core between the topsheet and the backsheet, the backsheet comprising the ink-printed substrate of claim 10.

16. An ink-printed substrate, comprising:
    a. a substrate pretreated with corona treatment, the substrate having a substrate surface tension of about 40 to about 45 dynes/cm;
    b. a water-based ink composition printed on the substrate; and
    c. an overprint varnish comprising between about 30% and about 60% of a polyurethane dispersion by weight of the overprint varnish, between about 3% and about 20% of a very low $Tg°$ C. water-based polymer by weight of the overprint varnish, and between about 1% and about 15% of a surfactant by weight of the overprint varnish;
        wherein the water-based ink composition comprises an average color density of at least about 0.48 or greater;
    wherein the ink-printed substrate comprises a Crockfastness-Loss-to-Density Ratio of about −1.0 to about −6.0.

17. The ink-printed substrate of claim 16, wherein the overprint varnish comprises a colloidal dispersion.

18. The ink-printed substrate of claim 16, wherein the substrate comprises one of a non-woven, a film, a polyolefin web, a fibrous polyolefin web, a cellulosic web, an elastomeric web or combinations thereof.

19. The ink-printed substrate of claim 16, wherein the ink printed substrate comprises an average crockfastness of at least about 2.5 or greater, according to the Crockfastness Measurement Method.

20. The ink-printed substrate of claim 16, wherein the water-based ink composition comprises a very low $Tg°$ C. water-based polymer component.

* * * * *